(12) United States Patent
Fuentes Aguilar et al.

(10) Patent No.: US 11,633,140 B2
(45) Date of Patent: Apr. 25, 2023

(54) SYSTEM, METHOD AND APPARATUS FOR ASSESSING AND MONITORING MUSCLE PERFORMANCE WITH SELF-ADJUSTING FEEDBACK

(71) Applicant: INSTITUTO TECNOLÓGICO Y DE ESTUDIOS SUPERIORES DE MONTERREY, Jalisco (MX)

(72) Inventors: Rita Quetziquel Fuentes Aguilar, Jalisco (MX); Alejandro Garcia Gonzalez, Jalisco (MX); Daniel Aragon Han, Jalisco (MX); Yoku Sashida Mendez, Jalisco (MX); Juan Carlos Vazquez Fuentes, Jalisco (MX)

(73) Assignee: INSTITUTO TECNOLÓGICO Y DE ESTUDIOS SUPERIORES DE MONTERREY, Monterrey (MX)

( * ) Notice: Subject to any disclaimer, the term of this patent is extended or adjusted under 35 U.S.C. 154(b) by 427 days.

(21) Appl. No.: 16/651,373

(22) PCT Filed: Feb. 15, 2019

(86) PCT No.: PCT/MX2019/000014
§ 371 (c)(1),
(2) Date: Mar. 27, 2020

(87) PCT Pub. No.: WO2019/209098
PCT Pub. Date: Oct. 31, 2019

(65) Prior Publication Data
US 2020/0289009 A1    Sep. 17, 2020

(30) Foreign Application Priority Data
Apr. 25, 2018  (MX) ............... MX/a/2018/005076

(51) Int. Cl.
*G16H 20/30*     (2018.01)
*A61B 5/316*     (2021.01)
(Continued)

(52) U.S. Cl.
CPC ............. *A61B 5/316* (2021.01); *A61B 5/389* (2021.01); *A61B 5/742* (2013.01); *G01R 29/12* (2013.01);
(Continued)

(58) Field of Classification Search
CPC ......... A61B 5/316; A61B 5/389; A61B 5/742; A61B 2505/09; A61B 5/0002;
(Continued)

(56) References Cited

U.S. PATENT DOCUMENTS 6,631,299 B1 * 10/2003 Patel .................... G05B 13/042
                                                     700/37
2006/0173364 A1    8/2006 Clancy et al.
(Continued)

FOREIGN PATENT DOCUMENTS

CN      1251289 A   *  4/2000
CN    105725990 A   *  7/2016  ........... A61B 5/0002
(Continued)

OTHER PUBLICATIONS

Patel et al., U.S. Pat. No. 6,631,299 B1, saee shortened version.*
(Continued)

*Primary Examiner* — Kandasamy Thangavelu
(74) *Attorney, Agent, or Firm* — Nixon & Vanderhye

(57) ABSTRACT

Disclosed is a system for assessing and monitoring muscle performance with self-adjusting feedback in order to evaluate progress in physiotherapy received by patients who have suffered muscle damage, the method including: A) at least one apparatus for acquiring muscle or biopotential signals; signal conditioning; processing, sending, receiving informa-
(Continued)

tion; and self-adjusting feedback; B) at least one external computer and/or monitor or graphic interface for viewing external information; C) wherein the at least one apparatus for acquiring muscle or biopotential signals; signal conditioning; processing, sending, receiving information; and self-adjusting feedback and the at least one external computer and/or monitor or graphic interface for viewing external information are configured to carry out a method for measuring, extracting and processing parameters for assessing and monitoring muscle performance with self-adjusting feedback in order to evaluate progress in physiotherapy received by patients who have suffered muscle damage.

20 Claims, 10 Drawing Sheets

(51) Int. Cl.
| | | |
|---|---|---|
| *G16H 40/67* | (2018.01) | |
| *G16H 50/50* | (2018.01) | |
| *G16H 15/00* | (2018.01) | |
| *G16H 50/70* | (2018.01) | |
| *G16H 50/20* | (2018.01) | |
| *G16H 40/40* | (2018.01) | |
| *A61B 5/00* | (2006.01) | |
| *G01R 29/12* | (2006.01) | |
| *G05B 15/02* | (2006.01) | |
| *G06Q 10/0631* | (2023.01) | |
| *A61B 5/389* | (2021.01) | |

(52) U.S. Cl.
CPC ....... *G05B 15/02* (2013.01); *G06Q 10/06316* (2013.01); *G16H 15/00* (2018.01); *G16H 20/30* (2018.01); *G16H 40/40* (2018.01); *G16H 40/67* (2018.01); *G16H 50/20* (2018.01); *G16H 50/50* (2018.01); *G16H 50/70* (2018.01); *A61B 2505/09* (2013.01)

(58) Field of Classification Search
CPC ...... A61B 5/1107; G01R 29/12; G05B 15/02; G06Q 10/06316; G16H 15/00; G16H 20/30; G16H 40/40; G16H 40/67; G16H 50/20; G16H 50/50; G16H 50/70; G16H 40/63; A61N 1/05; B61K 9/08; G01V 3/12; G06B 13/042
See application file for complete search history.

(56) References Cited

U.S. PATENT DOCUMENTS

| | | | | |
|---|---|---|---|---|
| 2008/0058913 | A1* | 3/2008 | Gray | ............ A61N 1/05 607/116 |
| 2016/0089573 | A1* | 3/2016 | House | ............ G16H 20/30 482/8 |

FOREIGN PATENT DOCUMENTS

| | | | | |
|---|---|---|---|---|
| CN | 105824050 A | * | 8/2016 | ............ G01V 3/12 |
| CN | 108426942 A | * | 8/2018 | ............ B61K 9/08 |
| PT | PT104882 | | 6/2011 | |
| WO | WO 0107112 A2 | * | 2/2001 | .......... A61B 5/1107 |
| WO | WO01/54563 | | 8/2001 | |
| WO | WO 2018140429 A1 | * | 8/2018 | ............ A61B 5/389 |

OTHER PUBLICATIONS

Google.com, "Formula Cheatsheet", Down loaded on Aug. 10, 2022.*
Gray et al., U.S. Patent Application Publication 2008/0058913 A1, see shortened version.*
House et al., U.S. Patent Application Publication 2016/0089573 A1, see shortened version.*
Wikipedia, "Self-tuning", downloaded on Aug. 10, 2022.*
Vandorn, V, "Fundamentals of self-tuning control", Jul. 2007.*
Rijnbeek et al.., "Minimum Bandwidth requirements for recording Pediatric Electro cardiograms", American Heart Association, 2001, Dec. 2010.*
International Search Report—PCT/MX2019/000014—dated Jun. 24, 2019.

* cited by examiner

SYSTEM, METHOD AND APPARATUS FOR ASSESSING AND MONITORING MUSCLE PERFORMANCE WITH SELF-ADJUSTING FEEDBACK

FIELD OF THE INVENTION

The present invention relates to the medical and health industry as a whole, it specifically relates to the field of therapeutic, rehabilitation, medical or sports devices, used in the measurement of physiological variables; such as display, monitoring and/or surveillance devices of several physiological aspects. More particularly, it relates to a system, method and apparatus for assessing and monitoring muscle performance with self-adjusting feedback.

BACKGROUND OF THE INVENTION

Regarding the field of the invention of therapeutic, rehabilitation or medical devices, it has been identified that the primary causes of the abandonment of physiotherapy are: difficulty in following or complying with the indications in their entirety, non-attendance at consultations, absence in the modification of habits and disappointment in the treatment due to lack of perception of progress. In accordance with the World Health Organization (WHO), "adherence is the degree to which a person's behavior corresponds to the recommendations agreed upon by a health care provider", additionally it has pointed out that increasing a patient's perception of improvement increases adherence to treatment, which can lead to better results.

There are teams dedicated to carrying out both passive and active therapies. These equipment are usually mechanical and are designed to perform therapies that are repetitive and that provide the movement that the patient needs with a force established by the physiotherapist.

At present, the comprehensive, precise and effective assessment of rehabilitation therapies is a topical issue and generally, there are few possibilities in devices, equipment or systems that allow an expert in rehabilitation, medicine or sports to have quantitative data to assess the initial condition of the patient and the progressive response in each session.

In particular, rehabilitation is assessed mainly through the measurement of mechanical variables such as range of motion. The range of motion reflected in the angles formed by the body segments involved in a joint, this variable can be determined statically with a goniometer and dynamically with an electrogoniometer or, if resources and access are available, with a motion capture system through infrared cameras. However, the electrophysiological assessment is even more limited. This can be done by recording the electrical activity of nerve and muscle fibers generated by any motion.

Devices that measure the electrical activity of muscle or nerve fibers usually only acquire, display and store the signals, in one or various groups of fibers, however, it is not possible to translate them into information interpreted as an assessment parameter. The assessment of this information allows the quantification of muscle activity and thus allowing decisions to be made concerning therapy or, in the case of a patient, verifying their electrophysiological state. It is commonly known in the field of healthcare that rehabilitation therapies usually take a long time to show a result that can be perceived by the patient, the improvement is often visible after months or sometimes years of therapy treatment hence, dropping out of therapy often occurs frequently. This is avoided when the patient has a quantitative assessment of their condition.

At present, there are other devices that independently or by their combination or comparison among them solve the problems previously described. By way of illustration and without limitation, the first type of device can be the electromyographs (EMG), which generally are devices that measure muscle activity, which use intramuscular or surface electrodes with a bandwidth of 0.1 to 10 kHz and are used in standard practice in the neuromuscular disease diagnosis, monitoring of muscle activation and motor control disorders, as well as in the development of prostheses and for the detection of muscle condition in areas that might or might not produce motion such as muscles associated with speech.

Another type of device may be, the nerve, motor and sensory conduction measurement equipment, commonly known in the field of expertise as "MNCS and NCS", which allow to study the conduction process of the nerve impulses along the motor and sensory nerve fibers to establish the level of commitment or conservation of the axons and their myelinic envelope within the peripheral nerve trunks which necessarily involve electrically stimulating the fibers.

Other devices may be electro-stimulators, which generally send a low-voltage, current-controlled electrical impulse and similarly cause muscle contraction to impulses sent by the central nervous system.

A search was made to determine the closest prior art, thus finding the documents below:

Patent application MX/a/2015/005567 by Ernesto Rodriguez Leal, as the inventor, dated Apr. 30, 2015, was found, which discloses a non-invasive mechatronic device that generates joint motricity using EEG and EMG signals with specific applications as a motor limb rehabilitator and/or limb movement assistant. The device is formed by at least one exoskeleton of rigid material and is associated with a given joint. It is electrically connected to a control system, which in turn is wirelessly connected to a set of EEG sensors and is in constant communication while the device is on; it is wired to at least one exoskeleton whose function is to assist in movement or rehabilitate one or more joints of the human body limbs.

Document MX/a/2012/007517 by Ivan Eric Ojeda Diaz dated Jun. 26, 2012, was found, which discloses a robot for physical rehabilitation of upper limbs. The robot can generate ten different movements and their combinations, allowing the rehabilitator to select speeds, directions of rotation, degrees of angular movements and number of automatic cycles obeyed by five integrated mechatronic sets to rehabilitate the upper limb at the three-dimensional points selected by the rehabilitator. The orders programmed by the rehabilitator are distributed as digital signals of activation and deactivation to the five mechatronic sets and translated into the controlled movement of their relevant motors by a Programmable Logic Controller that receives the manual digital orders by means of selectors, and the automatic ones using a Man Machine Interface. The robot has a structure built in extruded aluminum profiles that in its front part allows the assembly of an upper and lower rotating system for the movement in curved rail meridians which in turn load a sliding carriage by means of bearings. This carriage holds by means of cushioned parts the upper limb to be rehabilitated, left or right, and loads it and/or flexes it and/or rotates it in the degrees previously selected and previously tested in its cycle simulation function.

However, the devices of the said documents are meant to assist in movement or rehabilitate one or more joints of the human body limbs; but they do not allow assessing and monitoring muscle performance with self-adjusting feedback, through the identification of different biopotentials generated by muscle or nerve fibers in the upper or lower limb or head of any living being, with the aim of generating a quantitative monitoring of muscle performance of the users in various situations that can be in the sports, rehabilitation, therapeutic or medical field. Furthermore, they are not specifically designed for people who have not had mobility in their limbs for longer periods of time, causing them to lose muscle mass, and thus presenting signs of electrical activity that cannot be read conventionally.

The present invention was developed in response to the need for a system, method and apparatus for assessing and monitoring muscle performance with self-adjusting feedback that allows solving the aforementioned problems.

OBJECTIVES OF THE INVENTION

The present invention mainly aims at making available an innovative system, method and apparatus for assessing and monitoring muscle performance with self-adjusting feedback, by identifying different biopotentials, especially those generated by muscle or nerve fibers, which may be found in the upper or lower limb or head of any living being.

Another objective of the present invention is to make available said system, method and apparatus for assessing and monitoring muscle performance with self-adjusting feedback, which allows identifying different biopotentials preferably, but without being limited to, the information provided by the muscle or nerve fibers with electrical activity less than 0.001V that due to their disposition, injury or accessibility are not identified by other devices or apparatus, with the aim of generating a quantitative monitoring of users' muscle performance in various situations that can be in the sports, rehabilitation, therapeutic or medical field.

Another objective of the present invention is to make available an innovative system, method and apparatus for assessing and monitoring muscle performance with self-adjusting feedback, which also allows identifying electrical activity in injuries of the muscle or nerve fibers, by way of example and without being limited to a case of spinal trauma, total or partial paralysis among others and can establish a quantitative mechanism of user monitoring.

Another objective of the present invention is to make available an innovative system, method and apparatus for assessing and monitoring muscle performance with self-adjusting feedback, which also allows a thorough, frequent and non-invasive review of the user and which provides monitoring information to a third party who may be, but may not be limited to, an expert in the application field.

Another objective of the present invention is to make available an innovative system, method and apparatus for assessing and monitoring muscle performance with self-adjusting feedback, which also allows assessing the therapy received by patients with lower or upper limb damage after suffering a spinal injury or trauma, which allows the quantitative measurement of the muscle activity, providing this data for each patient in a visual way and the physiotherapist graphically and numerically; in addition to being able to save the results per session to compare them and measure improvements as percentages of increase, thus motivating the user to continue, and the physiotherapist can make decisions on the therapy applied to each patient.

And all those qualities and objectives that will become apparent when disclosing the present invention supported by the depicted embodiments.

BRIEF DESCRIPTION OF THE INVENTION

The main technical problem is the reading of signals coming from a degenerated muscle, having to establish characteristics inherent in particular users. Then, an electric circuit was built comprising a medical instrumentation scheme, where the sensors are surface electrodes (non-invasive), the analogical conditioning is done in accordance with the specific characteristics of the patients and with the requirements of the physiotherapist, and its output is shown in a cell phone application, in a PC or another portable device. The device is a tool for the health professional that allows them assessing and re-assessing the sessions with the patient, as well as monitoring the improvement quantifiably.

Another problem it solves is the monitoring of the patient throughout the therapy, the statistics of activity in the desired period, and an element of motivation for the patient not to give up the therapy sessions, and instead may view the progress without this depending on the personal perception.

Overall, the innovative system for assessing and monitoring muscle performance with self-adjusting feedback in accordance with the present invention comprises:

A) At least one apparatus for acquiring muscle or biopotential signals; signal conditioning; processing, sending, receiving information; and self-adjusting feedback;

B) At least one external computer and/or monitor or graphic interface for viewing external information;

C) Wherein said at least one apparatus for acquiring muscle or biopotential signals; signal conditioning; processing, sending, receiving information; and self-adjusting feedback and said at least one external computer and/or monitor or graphic interface for viewing external information, are configured to carry out a method for extracting and processing the monitoring parameters.

Said apparatus for acquiring; conditioning; processing, sending, receiving information; and self-adjusting feedback in one of its preferred embodiments comprises an on/off button, a reset button; optionally it comprises several visual information indicators such as leds and LCD and/or touch screen; alternatively, it may comprise at least three inputs for the biopotential sensors; an input for external storage device, either by SD, micro SD, USB-type card.

Another embodiment of the device for acquiring; conditioning; processing, sending, receiving information; and self-adjusting feedback can dispense with some or all of the several visual information indicators such as leds and/or any type of screen; and the various types of external storage devices, either by external SD, micro SD, USB-type card, among others; and may include a greater number of inputs for biopotential sensors.

Said at least one apparatus for acquiring muscle or biopotential signals; signal conditioning; processing, sending, receiving information; and self-adjusting feedback comprises (A) a first module for acquiring biopotentials or signals, a second module for analog/electronic conditioning of biopotentials or signals, a third module for processing biopotentials or signals, sending and receiving information with feedback with the first module, and a fourth module for sensory display or feedback of the information.

Said first module for acquiring biopotentials or signals comprises at least two or more biopotential sensors such as surface mount electrodes, preferably non-invasive, with which the biopotentials are recorded.

Recording is achieved by implementing at least one differential mode amplifier where the two or more active electrodes and a reference electrode are connected. Moreover, the differential amplifier contains at least one component and/or potentiometer capable of modifying its impedance value manually or electronically, as shown in equation 1:

$$|z| = \sqrt[2]{R^2 + XJ^2} \quad \text{Equation 1}$$

Wherein z is the nominal value of the impedance,
R the resistive value,
X the reactance value, and
J is the imaginary unit and works as an adjustable gain dependent on the value of z.

Said differential amplifier is connected directly via cables or wires to the said second conditioning module.

Said second module for analog/electronic conditioning of the biopotentials or signals is integrated, but is not limited to, a set of analog band-pass type electronic filters, which aim at limiting the bandwidth of the differential signal in a range of approximately 0.001 to 250 Hz using preferably a margin of 5 to 99 HZ, which no other apparatus has presented before. Similarly, a threshold or voltage offset compensation circuit is integrated, commonly known as "offset", which allows adding constant and/or variable voltage values in such a way that the filtered signal only has positive components. Said compensation module exists before a negative-positive connection of the conditioning circuits, while it has no effect when the conditioning circuits are connected in a merely positive way.

This module is connected directly to the third module for processing, sending and receiving information.

Said third module for processing, sending and receiving information receives the voltage-compensated signal and comprises, but is not limited to; at least one 8 to 64-bit microcontroller or processor; one or more internal memories, one or more external memories, RAM, ROM; one or more indicators; one or more analog, digital ports; analog-to-digital (ADC), digital-to-analog (DAG) converters for feedback to the first module; communication circuits using wireless protocols such as Bluetooth, Wi-Fi, among others, for communicating with at least one external computer and/or monitor or graphic interface which may be, but are not limited to, a computer, cell phone or tablet for viewing or displaying the information. At least one of the ADCs is used to digitize the voltage-compensated signal and be stored in some of the memories, to later calculate the maximum value in the samples equivalent to one cycle and/or period of electrical activity and/or muscle contraction and/or activation of muscle or nerve fibers.

If in the said calculation, the maximum of the samples does not exceed a minimum threshold selected or preconfigured in the apparatus, then the processor or microcontroller modifies the value of z in the differential amplifier of the acquisition module in order to automatically adjust the amplitude of the biopotentials.

Said adjustments are made in (Vin) (1+|z|) type increments wherein Vin is the biopotential voltage.

Once the threshold is exceeded, the digitized signal is transmitted and received by the external computer and/or a monitor or graphic interface which can be, but is not limited to, a computer, cell phone or tablet for viewing or displaying the information. Moreover, the said module controls the fourth module for sensory display or feedback.

The fourth module for sensory display or feedback is controlled by the 8 to 64-bit microcontroller or processor of the third module for processing, sending and receiving information. It comprises a set of forms for the display of information, which may or may not include and are not limited to: a plurality of leds, buttons, lights; screens or LCD, OLED and/or 7-segment display. The purpose of said module is to provide information to the user, which may include, but not be limited to: the different phases of the method; use, operation, manipulation and/or errors concerning the apparatuses.

Once the signal has been sent to the external computer and/or monitor or graphic interface for viewing external information (B) such as, but without being limited to, a computer, cell phone or tablet, it may be viewed by the individual through an embedded and/or native web application in the computer, which will display different types of information such as, but without being limited to the biopotential without conditioning, the signal with analog conditioning, voltage compensation, self-adjusting gain, session time and said information will be displayed on the monitor and/or interface.

Said information may at the same time be stored in the external memory of the apparatus of the present invention, as well as in the external computer for monitoring and quantitative assessment purposes. Moreover, the user may modify several parameters that will be sent to the processing module for the adjustment of the biopotential record.

The information generated by the invention is used in the machine learning technique to suggest optimizations of use, therapies, exercises, among others.

The method for measuring, extracting and processing the parameters for assessing and monitoring muscle performance with self-adjusting feedback in order to evaluate progress in physiotherapy received by patients who have suffered muscle damage, consisting of:

a) Placing at least two or more biopotential sensors such as surface mount electrodes, preferably non-invasive, for recording the reading of signals from the muscle and/or nerve fibers, of at least one apparatus for acquiring muscle or biopotential signals; for signal conditioning; signal processing, sending and receiving information; and self-adjusting feedback;

b) Selecting at least one external computer and/or monitor or graphic interface for viewing external information and several recording parameters from said at least one apparatus for acquiring muscle or biopotential signals; for signal conditioning; for signal processing, sending and receiving information; and self-adjusting feedback, which are, but are not limited to, sampling duration and/or time, session number, calibration, initial amplification value; type of user (with or without muscle damage), injury, among others;

c) Recording the reference signals or biopotential, if it is the first time it is used it will serve as a calibration parameter;

d) Calculating, in a module for processing of the apparatus, the maximum of one sample equivalent to a reference cycle of contraction or electrical activity;

e) Exceeding the calibration or preconfigured and/or selected threshold from the computer system and/or a monitor or graphic interface for viewing external information.

f) Adjusting the potentiometer gain, (Vin) (1+|z|)

g) Re-recording the signal as in step c), which is called digital control loop amplification;

h) Sending the information to the external computer and/or monitor or graphic interface for viewing external information;

i) Calculating the assessment and monitoring indicators as: percentage increase or decrease, which is the difference of the calibration value minus the maximum value of the current sample divided by the calibration value;

j) Applying a variety of FIR and/or IIR type filters for the averaging of the information;

k) Calculating the indicators by means of the calculation of discrete integrals; and;

l) Applying machine learning or deep learning techniques.

For a better understanding of the characteristics of the present invention, the drawings described below, by way of example and without limitation, are attached to this description as an integral part thereof.

Figure 1:
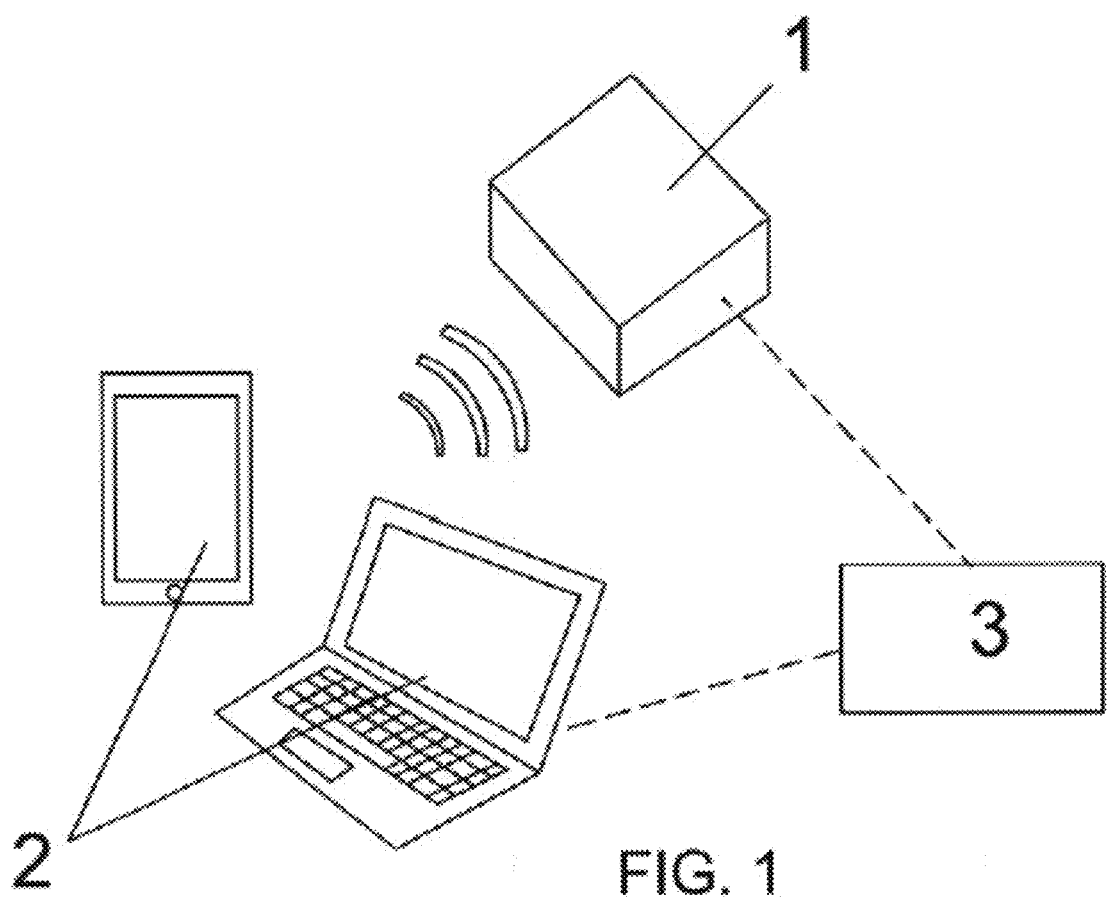
FIG. 1 depicts the image of one of the embodiments of the system for assessing and monitoring muscle performance with self-adjusting feedback, in accordance with the present invention.

For a better understanding of the invention, a detailed description of some of its embodiments thereof will be made, shown in the drawings that are attached to this description by way of example and without limitation.

DETAILED DESCRIPTION OF THE INVENTION

The characteristic details of the system, method and apparatus for assessing and monitoring muscle performance with self-adjusting feedback are clearly shown in the following description and the accompanying illustrative drawings, with the same reference signs serving to point out the same parts. Those skilled in the art will recognize that alternatives or potential variations of the invention may be generated within the scope of the same claims being made.

The embodiments of the invention described herein are not limitative whatsoever, but rather illustrative. It shall not be understood that the embodiments of the described invention are necessarily unique, preferred or to be interpreted literally.

Figure 2:
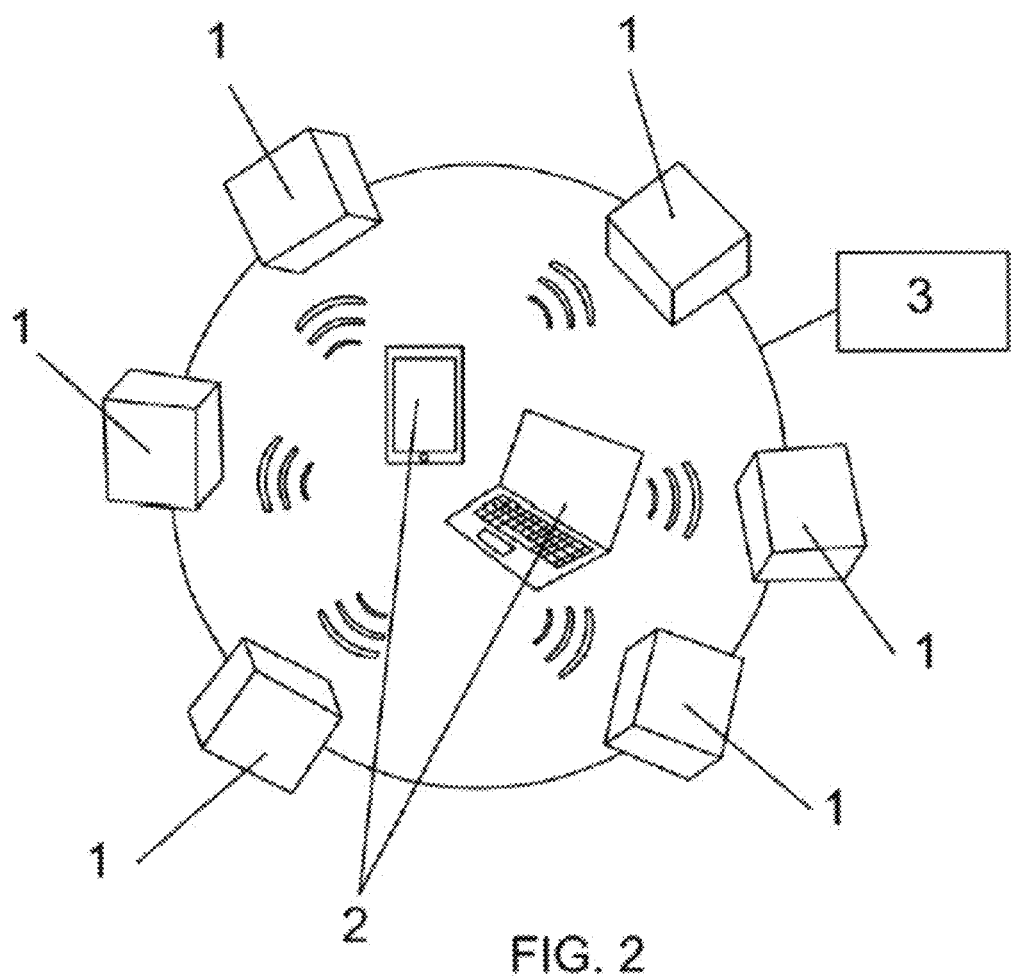
FIG. 2 depicts the image of another embodiment of the system for assessing and monitoring muscle performance with self-adjusting feedback, in accordance with the present invention.

Referring to FIGS. 1 and 2; the system for assessing and monitoring muscle performance with self-adjusting feedback in accordance with the present invention comprises at least one apparatus (1) for acquiring; conditioning; processing, sending, receiving information; and self-adjusting feedback; at least one external computer and/or a monitor and/or graphic interface (2) for viewing information; wherein said at least one apparatus (1) for acquiring muscle or biopotential signals; signal conditioning; processing, sending, receiving information; and self-adjusting feedback and said at least one external computer and/or monitor and/or graphic interface (2) for viewing external information are configured to carry out a method for extracting and processing the monitoring parameters (3).

Said system is capable of synchronizing and/or connecting to at least one apparatus (1) for acquiring; conditioning; processing, sending, receiving information; and self-adjusting feedback with an external computer and/or external computer and/or monitor and/or graphic interface (2) for viewing external information, which may include tablets, cell phones, computers, laptops, and other technologies.

Figure 3:
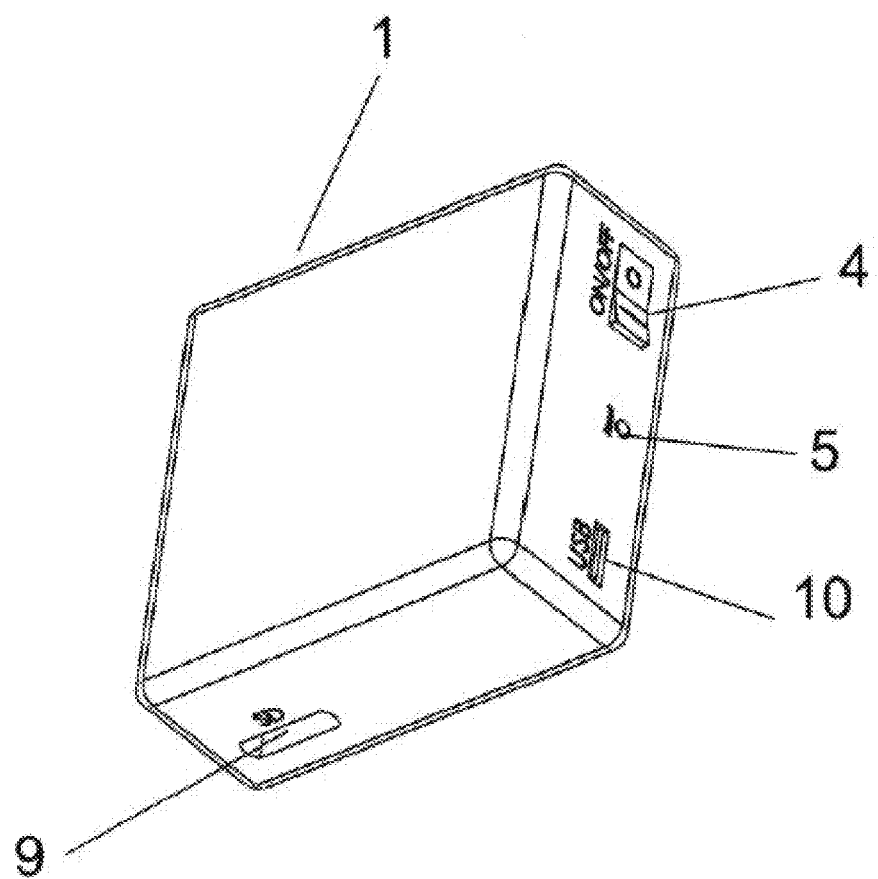
FIG. 3 depicts in conventional perspective the apparatus for acquiring; conditioning; processing, sending, receiving information; and self-adjusting feedback.
Figure 4:
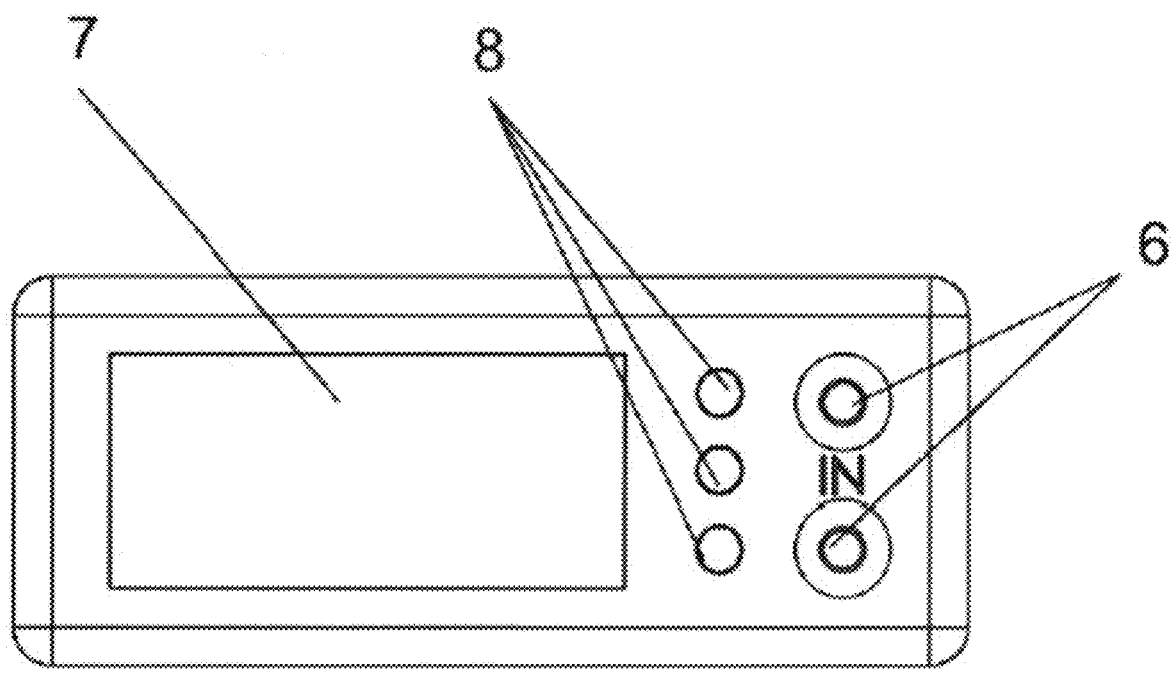
FIG. 4 depicts a back view of the apparatus for acquiring; conditioning; processing, sending, receiving information; and self-adjusting feedback.

Referring to FIGS. 3 and 4, the apparatus (1) contains a plurality of buttons such as an on/off button (4), a reset button (5); several visual information indicators such as leds (8) and LCD and/or touch screen (7); at least two inputs (6) for the biopotential sensors; an input for external storage device, either by SD or microSD-type card (9), and a USB input (10).

Another embodiment of the apparatus for acquiring; conditioning; processing, sending, receiving information; and self-adjusting feedback may dispense with some or all of the several visual information indicators such as leds and/or any type of screen; and the various types of external storage devices, whether by external SD, micro SD, USB-type card, among others.

Another embodiment of the apparatus for acquiring; conditioning; processing, sending, receiving information; and self-adjusting feedback may include a greater number of biopotential sensor inputs.

Figure 5:
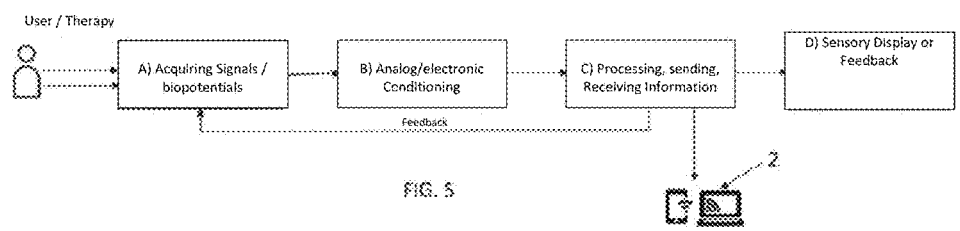
FIG. 5 depicts the block diagram of the apparatus for acquiring; conditioning; processing, sending, receiving information; and self-adjusting feedback.

Referring to FIG. 5, the apparatus (1) for acquiring muscle or biopotential signals from a patient undergoing therapy; signal conditioning; processing, sending, receiving information; and self-adjusting feedback generally comprises four modules, which are A). A first module for acquiring signals or biopotentials; 8). A second module for analog/electronic conditioning, C). A third module for processing, sending and receiving information and D.) A fourth module for sensory information display (Feedback). The third module for processing, sending and receiving information (C) allows communication with the external computer and/or monitor and/or graphic interface (2).

Figure 6:
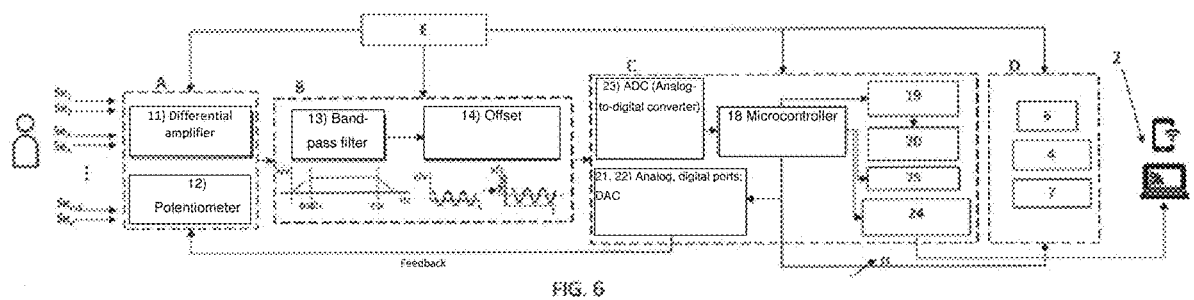
FIG. 6 depicts the block diagram in detail of the apparatus for acquiring; conditioning; processing, sending, receiving information; and self-adjusting feedback.

Referring to FIG. 6, said first module for acquiring signals or biopotentials (A) comprises at least two or more biopotential sensors called [Se1, Se2, Se3 . . . Sn-1, Sen], which can be, but are not limited to, Ag/AgCl surface mount electrodes, preferably non-invasive, with which the biopotentials are recorded, mainly of the surface electrical activity. In this embodiment of the apparatus, the recording is achieved through an oxide/reduction process of the sensors, where the ionic current is converted into electric current and acquired by at least one differential mode amplifier (11) with a common mode rejection greater than 100 dB. In said differential mode amplifier (11), the two or more biopotential sensors called [Se1, Se2, Se3 . . . Sn-1, Sen] are connected.

Moreover, in said acquisition of signals or biopotentials (A), the differential mode amplifier (11), contains at least one resistive, capacitive component or integrated circuit, called potentiometer (12), capable of modifying its impedance value manually or electronically, in the form)

$$|z| = \sqrt[2]{R^2 + XJ^2}$$

wherein z is the nominal value of the impedance, R the resistive value, X the reactance value and J the imaginary unit and works as an adjustable gain dependent on the value of z. The value of z is modified by the microcontroller automatically, up to the point where the value of the biopotential exceeds the pre-set threshold from the external computer and/or monitor and/or graphic interface (2) of the reading in accordance with the area expert.

The first module for acquiring signals or biopotentials (A) is capable of automatically adjusting the signal gain in the range of [1-100,000] V/V. Said gain adjustment value is an indicator used in the external computer and/or monitor and/or graphic interface (2) for viewing external information, for the application of machine learning and/or deep learning techniques commonly known in the prior art as "machine learning" and "deep learning", respectively. The first module for acquiring signals o biopotentials (A). is preferably implemented at a range of [10-10,000] V/V and is directly connected through cables or wires to the second module for analog/electronic conditioning (B).

The second module for analog/electronic conditioning of the biopotentials and/or signals (B) is integrated by a set of electronic band-pass filters (13), which aim at limiting the bandwidth of the differential signal in an approximate or predetermined range. The preferential filters of this module are those designed with polynomial and Butterworth configuration and structure with second order Sallen Key. Other embodiments may implement a variety and diversification of configurations and topologies, such as: Bessel, Tschebyscheff, Rauch and even being of a higher order.

Said second module for analog/electronic conditioning of biopotentials and/or signals (B) is characterized by a bandwidth of 0.001 to 250 Hz using preferably a range of 5 to 99 HZ, which no other apparatus has presented before.

Figure 7:
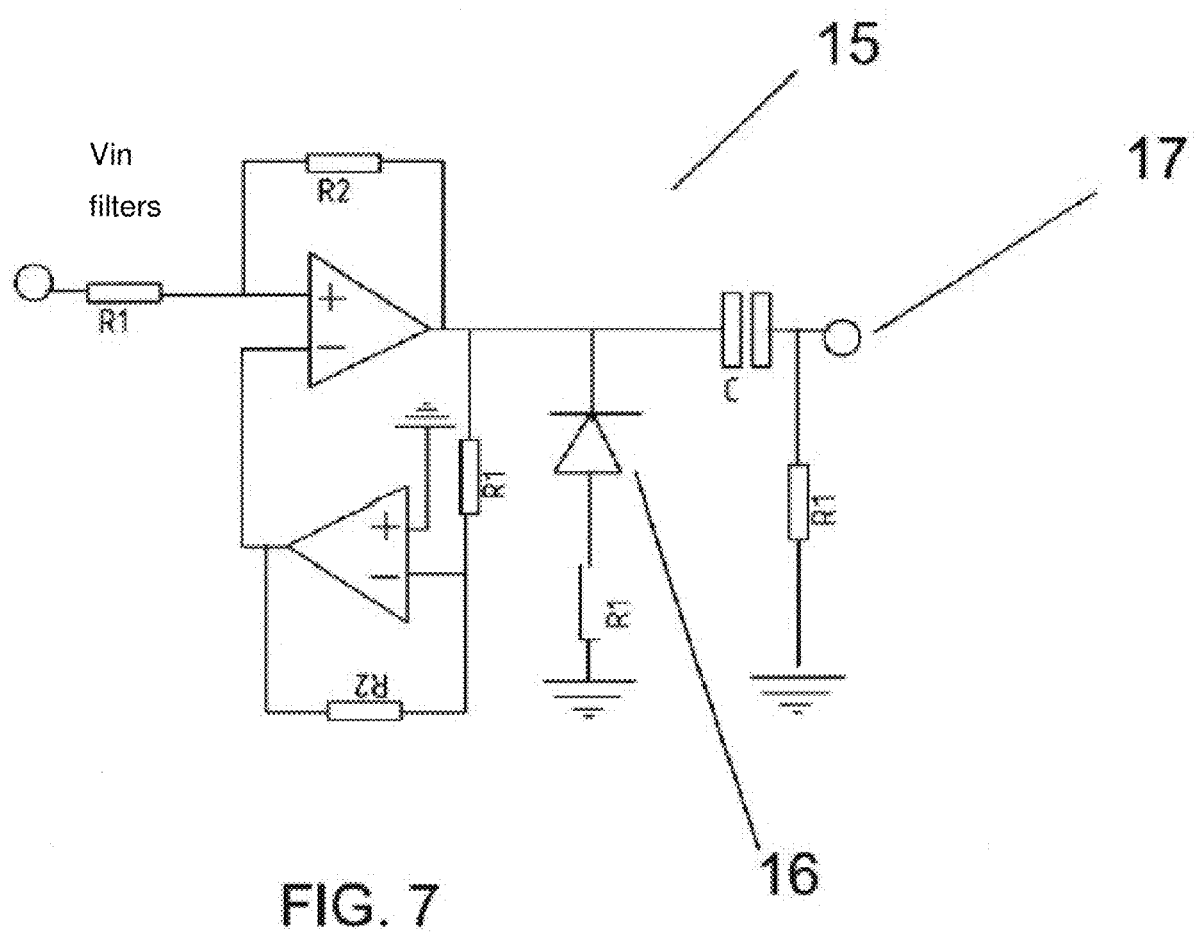
FIG. 7 depicts the schematic diagram of the voltage compensation module of the apparatus for acquiring; conditioning; processing, sending, receiving information; and self-adjusting feedback in one of the embodiments of the invention.

Moreover, said second module for analog/electronic conditioning of the biopotentials and/or signals (B), includes a threshold or voltage offset compensation circuit (14), commonly known as "offset" which allows adding constant and/or variable voltage values in such a way that the filtered signal has only positive components. This is accomplished by configuring a feedback circuit (15) of the average of the filtered signal plus a fixed voltage value, such as, but without being limited to, the circuit depicted in FIG. 7 with a Zener diode (16) of 0.7-1V offset. The output of the compensation circuit (17) is connected directly to the third module for processing, sending and receiving information (C).

Figure 8:
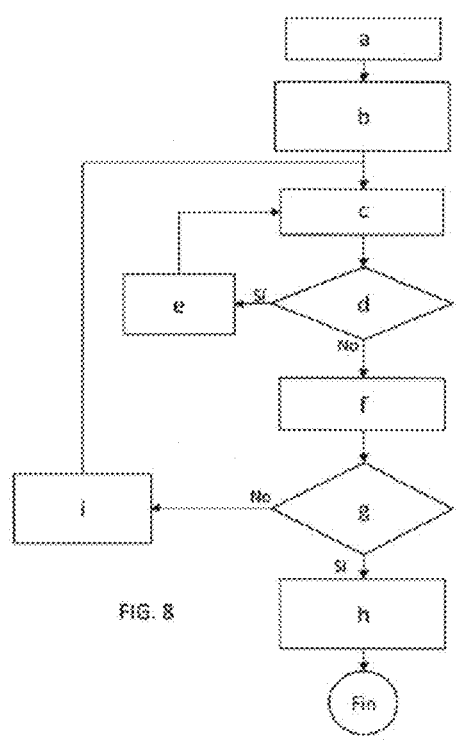
FIG. 8 depicts a flowchart of the method for extracting the information from the apparatus, acquiring; conditioning; processing, sending, receiving information; and feedback.

Referring to FIGS. 6 and 8, the third module for processing, sending and receiving information (C) receives the voltage-compensated signal and comprises, but is not limited to; at least one 8 to 64-bit microcontroller or processor (18); one or more internal memories (19), one or more external memories (20), USB, RAM, ROM; one or more analog and digital ports (21) and digital-to-analog converters (DACs) (22); analog-to-digital converters (ADCs) (23); wireless protocols communication circuits (24) such as Bluetooth, WIFI, among others, as depicted in the figure.

At least one of the analog-to-digital converters (ADCs) (23) is used to digitize the voltage compensated signal, where the preferred digital conversion resolution is 8 to 12 bit, but may be higher in accordance with the capabilities of the 8 to 64-bit microcontroller or processor (18) selected in the several potential embodiments of the third module for processing, sending and receiving information (C).

Subsequently, the 8 to 64-bit microcontroller or processor (18), checks if it was configured as the first session, if so, uses the information as calibration parameters and generates the indicators (25). Otherwise, since it is not the first session, it digitizes the compensated signal y [n] during the time [T], a parameter configurable from the external computer and/or a monitor and/or graphic interface (2) for viewing external information. Subsequently, and in the particular case, it makes a copy of the information y [n] in the internal memory (19) SD, microSD-type, and/or in the external memory (20) USB, RAM and/or ROM.

Thereupon, the 8 to 64-bit microcontroller or processor (18) performs the calculation to determine the maximum value [M] of y [n]. If the value [M] exceeds a threshold [U]. determined by the area expert, the information y [n] is sent to the external computer and/or monitor and/or graphic interface (2) for viewing external information via wireless protocols communication circuits (24) such as, but without being limited to, Bluetooth or Wi-Fi technology. Otherwise, the gain is adjusted by means of the potentiometer (12) in the first module for acquiring signals o biopotentials (A) is adjusted in the above-mentioned range from 1 to 100,000 V/V, in accordance with the function (Vin) (1+|z|), wherein Vin is the voltage of the biopotential and z the function described in the first module for acquiring signals o biopotentials (A). The threshold range can be [0.1 to 0.000001] V, preferably [0.001 to 0.000001] V, but may vary in some other embodiment of the apparatus (1).

Moreover, the calibration parameters, initial gain adjustment, sampling time, duration and/or session number, threshold value and/or firmware update can be modified by the wireless protocols communication circuits (24) such as, but without being limited to, Bluetooth or Wi-Fi technology selected or configurable from the external computer and/or monitor and/or graphic interface (2) for viewing external information.

Both the information from [M], [U], y [n], aim at being used in the external computer and/or monitor and/or graphic interface (2) for viewing external information, for the application of machine learning and/or deep learning techniques.

Finally, the fourth module for sensory information display (D), is controlled by the third module for processing, sending and receiving information (C), which by pressing the on/off button (4), updates the leds (8), lights and/or LCD and/or touch screen (7) in accordance with the step being executed by the method for extracting information which may include, but not be limited to: the methods of using, operating, manipulating and/or errors concerning the invention.

The four modules are powered from a power source (E) as depicted in FIG. 6.

According to FIG. 8 the method for extracting the information from the apparatus, acquiring; conditioning; processing, sending, receiving information; and feedback starts with the placement of the sensors (a), then proceeds with the selection of the parameters in the computer (b) to then record the signals or biopotentials (c), if it is the first session (d) then the calibration data are saved (e) and returns to letter "c", if it is not the first session, then the maximum equivalent sample is calculated (f); if the sample exceeds the threshold M>U (g) then information is sent to the computer y [n] (h); but if the threshold is not exceeded, then the potentiometer gain is adjusted (i) returning to letter "c".

Figure 9:
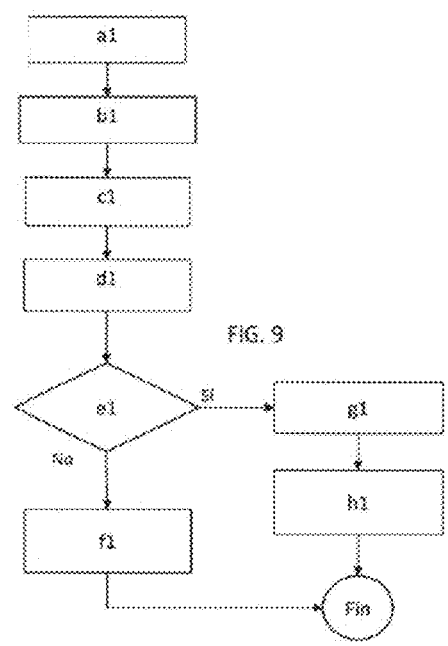
FIG. 9 shows a flowchart of the method of the external computer in one of the embodiments of the invention.

Regarding FIG. 9, the external computer and/or monitor and/or graphic interface (2, see FIGS. 1 and 2) for viewing external information, once switched on, it will seek to synchronize (a1) at least one of the embodiments of the apparatus (1, see FIG. 2) for acquiring; conditioning; processing, sending, receiving information; and self-adjusting feedback. When the first connection is successful, n-number of apparatuses may be connected at the expert's discretion. Subsequently, the signal recording parameters (b1) will be configured as they may be, but without being limited to: Time and/or duration of the recording, initial gain adjustment, session number, type of patient (healthy, injury), recording area, among others.

Subsequently, the sample (c1) is taken and the method previously described is initiated, referring to FIG. 8. Once the information y [n] has been received (d1) by the external computer and/or monitor and/or graphic interface (2, see FIGS. 1 and 2) for viewing external information, it will be checked if there is a previous (e1) session [#s]. In the event that there is no previous session [#s<0], all the information will be stored as reference parameter M [0]=y[n] (f1). Otherwise, when there is already a previous session, the information is stored in a specific space as M[#s, n] and the diversity of indicators will be calculated (g1). Finally, the information of the indicators (h1) is displayed which can be viewed by the user using an embedded web application and/or native in the computer.

Figure 10:
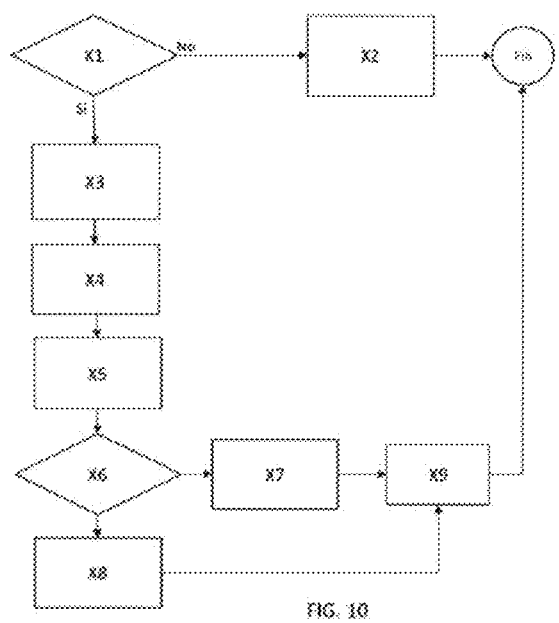
FIG. 10 depicts a flowchart of the method for calculating the indicators of improvement and/or deterioration in one of the potential embodiments of the invention.
Figure 11:
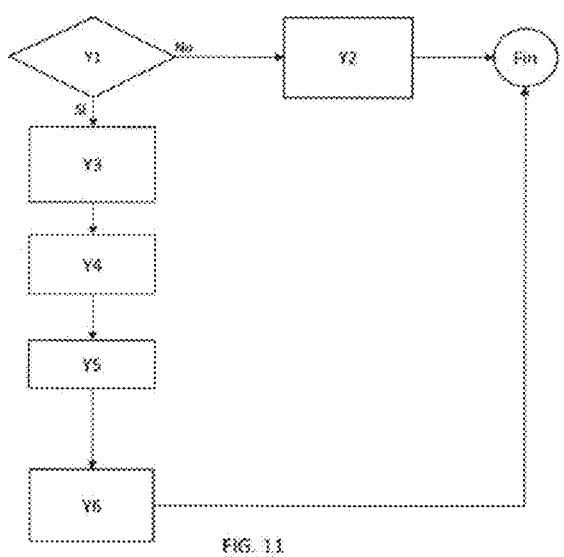
FIG. 11 shows a flowchart of the method for calculating the indicators of digital filters type FIR and/or IIR in one of the potential embodiments of the invention.
Figure 12:
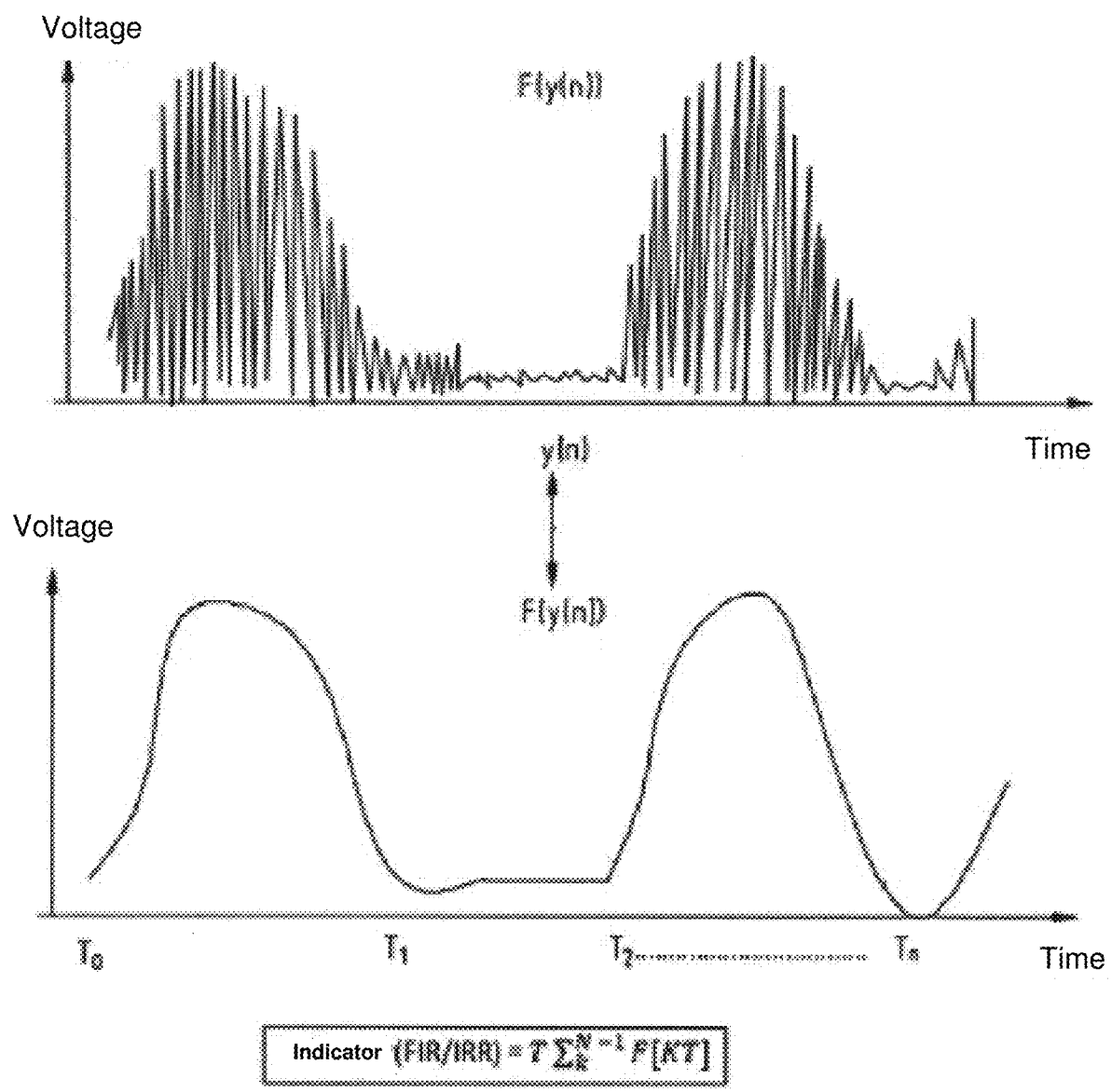
FIG. 12 depicts an example graph of the results of the method for extracting information and the calculation of the digital filter indicators in a possible embodiment of the invention.

The calculation of the indicators takes place in two sub-processes, regarding FIGS. 10, 11 and 12.

In the case of improvement or deterioration indicators, first it is determined whether there is a previous session #s>0 (x1), if there is not then the pre-processed signal is saved in memories M [n]=y [n] (x2); if there is already a previous session then the information received will be stored in M [#s, n]=y [n] (x3) and the counter of previous sessions will be increased by counting the number of sessions z[n] (x4). The difference between the current session and the previous one will be calculated (x5), z[n]=y[n]−(M [s−1], n]). The sign in z[n] (x6) is determined and in the event of a positive sign in the difference, the percentage of improvement % n [n]=(100−M [#s−1, n][100])/y[n] (x7) is calculated.

Otherwise, the deterioration percentage % h [n]=(100−M [#s, n] [100])/y [n−1] (x8). Finally, the indicators are stored in memory (x9).

In the case of indicators coming from the several FIR/IIR filters applied (FIG. 11), first it is determined whether there is a previous session (Y1), if there is not then the pre-processed signal is saved in memory M[0]=y[n] (Y2), if there is already a previous session then the session is saved in memory M[#s, n]=y [n] (Y3). The information is smoothed or filtered (Y4) by some kind of FIR and/or IIR (Finite Impulse Response/Infinite Impulse Response) filter, which can be, but without being limited to, Kalman, autoregressive, Mean Motion, among others. Later, the area under the curve of the signal F(y [n]) (Y5) is calculated, thereby an indicator (FIR/IIR)=$T\Sigma\_k^{\wedge}(N-1)$ [(F[KT])] (Y6) will be obtained. Such calculation may differ in any other embodiment of the invention and may include, but not be limited to the use of integration methods such as a method by rectangles, trapezoids, Adams, Simpson, among others.

Said indicators of improvement or deterioration and indicators (FIR/IIR) are used in the implementation of machine learning techniques. Moreover, with the extensive use of the invention a historical profile of the user is created.

FIG. 12 depicts a graph that exemplifies the results of the method for extracting information and the calculation of the digital filter indicators in a potential embodiment of the invention.

Figure 13:
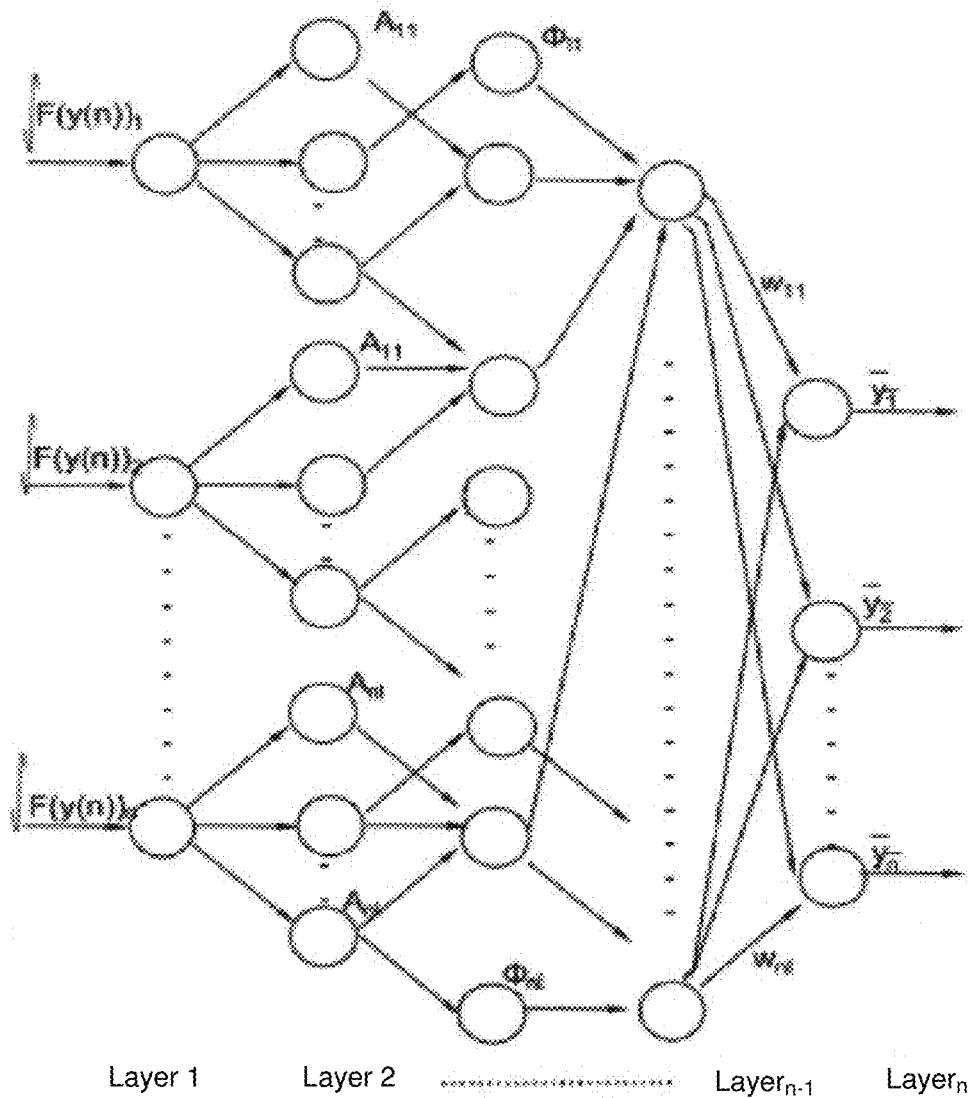
FIG. 13 depicts one of the potential implementations of the indicator information by means of the application of neural networks which may be, but without being limited to, suggesting to professionals or experts modifications in the exercises of activation, assessment and monitoring of the user's muscle performance.

Finally and regarding FIG. 13 and without limitation, the indicators previously described: y [n], gain adjustment, time and number of session, type of exercise, therapy and the information provided by the expert are used by machine learning techniques such as, neural networks by supervised and/or unsupervised learning, convolutional networks, diffuse and/or neurodiffuse systems, parametric identification and/or non-parametric identification, linear or polynomial regressions among others, are used to offer the system optimizations, improvements in use, gain adjustment, duration of exercise and/or therapy, variation of parameters or constants in the FIR and/or IIR filters.

It is believed that the invention has been sufficiently described so that a person with average knowledge in the field can reproduce and obtain the results mentioned in the present invention. However, any person skilled in the field of art covered by the present invention may be able to make modifications not described in the present application; however, if for the application of these modifications in a given structure or in the manufacturing process thereof, the matter claimed in the following claims is required, said structures must be included within the scope of the invention.

The invention claimed is:

1. An apparatus for evaluating progress in physiotherapy received by patients who have suffered muscle damage, the apparatus comprising;
   a first module for acquiring muscle or biopotential signals;
   a second module for analog/electronic conditioning of the muscle or biopotential signals;
   a third module for processing the muscle or biopotential signals, and for sending and receiving information of the muscle or biopotential signals with feedback with the first module; and
   a fourth module for display or feedback of the information of the muscle or biopotential signals,
   wherein the first, second, third, and fourth modules are powered from a power source,
   wherein said second module comprises:

a set of analog band-pass-type electronic filters that limit a bandwidth of a differential signal to a range of approximately 0.001 to 250 Hz; and a threshold voltage or voltage offset compensation circuit configured to add values of constant and/or variable voltages so that the filtered signal has only positive components, and wherein an output of the compensation circuit is connected directly to the third module.

2. The apparatus of claim 1,
wherein said first module for acquiring the muscle or biopotential signals comprises at least two or more biopotential signal sensors, wherein recording of the signals is achieved by implementing at least one differential mode amplifier in which two or more active electrodes and a reference electrode are connected, wherein the differential mode amplifier contains at least one potentiometer capable of modifying its impedance value manually or electronically, in accordance with the equation:

$$|z| = \sqrt[2]{R^2 + XJ^2}$$

where
z is the nominal value of the impedance,
R is the resistive value,
X is the reactance value, and
J is the imaginary unit and works as an adjustable gain dependent on the value of z, and wherein said differential mode amplifier is connected directly via cables or wires to said second conditioning module.

3. The apparatus of claim 2, wherein the at least two or more biopotential signal sensors are surface mount electrodes.

4. The apparatus of claim 1, wherein the apparatus is configured to receive more than two muscle or biopotential signals.

5. The apparatus of claim 1, wherein said third module receives a voltage-compensated signal and comprises:
at least one 8 to 64-bit microcontroller or processor;
one or more memories selected from the group of internal memories, external memories, RAM, and ROM;
one or more indicators;
one or more of analog and digital ports;
analog-to-digital converters (ADCs) and digital-to analog converters (DACs) for feedback to the first module; and
wireless protocols communication circuits for communicating with at least one external computer and/or monitor or graphic interface selected from the group consisting of a computer, a cell phone, and a tablet, for viewing or displaying information,
wherein at least one of the ADCs digitizes the voltage-compensated signal, which is stored in one or more of the memories to calculate a maximum value in the acquired muscle or biopotential signal samples during one cycle and/or a period of electrical activity and/or muscle contraction and/or activation of muscle or nerve fibers.

6. The apparatus of claim 5, wherein the external computer and/or a monitor or graphic interface transmits and receives the digitized signal when the digitized signal exceeds a minimum threshold selected or pre-configured in the apparatus.

7. The apparatus of claim 5, wherein the wireless protocols communication circuits are selected from Bluetooth and Wi-Fi.

8. The apparatus of claim 1, wherein said fourth module is controlled by an 8 to 64-bit microcontroller or processor of the third module.

9. The apparatus of claim 8, wherein the fourth module includes one or more selected from the group consisting of: LEDs, buttons, lights, an LCD display, and an OLED display, for the display or feedback of the information to a user.

10. The apparatus of claim 8, wherein the information provided by the fourth module includes one or more selected from the group consisting of the different phases of operating, using, manipulating, and/or errors concerning the apparatus.

11. The apparatus of claim 1, wherein the bandwidth of the differential signal is limited to a range of 5 to 99 HZ.

12. An apparatus for evaluating progress in physiotherapy received by patients who have suffered muscle damage, comprising:
a first module for acquiring muscle or biopotential signals;
a second module for analog/electronic conditioning of the muscle or biopotential signals;
a third module for processing the muscle or biopotential signals, and for sending and receiving information with feedback with the first module; and
a fourth module for display or feedback of sensory or nerve conduction information,
wherein the first, second, third, and fourth modules are powered from a power source,
wherein such third module receives a voltage-compensated signal and comprises
at least one 8 to 64-bit microcontroller or processor,
one or more memories selected from the group of internal memories, external memories, RAM, and ROM,
one or more indicators,
one or more of analog and digital ports,
analog-to-digital converters (ADCs) and
digital-to-analog converters (DACs) for feedback to the first module, and
wireless protocols communication circuits for communicating with at least one external computer and/or monitor or graphic interface selected from the group consisting of a computer, a cell phone, and a tablet, for viewing or displaying information,
wherein at least one of the ADCs digitizes the voltage-compensated signal which is stored in one or more of the memories to later calculate a maximum value in the acquired muscle or biopotential signal samples during one cycle and/or a period of electrical activity and/or muscle contraction and/or activation of muscle or nerve fibers,
wherein recording of the signals is achieved by implementing at least one differential mode amplifier,
wherein the differential mode amplifier contains at least one potentiometer capable of modifying its impedance value z manually or electronically,
wherein the microcontroller or processor is configured such that if the maximum value in the acquired muscle or biopotential signal samples does not exceed a minimum threshold selected or pre-configured in the apparatus, then the microcontroller or processor modifies the impedance value z in the differential mode amplifier of the first module in order to automatically adjust the amplitudes of the conditioned muscle or biopotential signal samples, and wherein said adjustments are made in (Vin) (1+|z|) type increments, wherein Vin is the voltage of the acquired muscle or biopotential signal samples.

13. The apparatus of claim 12, wherein the external computer and/or monitor or graphic interface transmits and receives the digitized signal when the digitized signal exceeds the minimum threshold selected or pre-configured in the apparatus.

14. A method for measuring, extracting, and processing parameters for assessing and monitoring muscle performance with self-adjusting feedback in order to evaluate progress in physiotherapy received by patients who have suffered muscle damage, the method comprising:
- A) Placing at least two or more biopotential signal sensors for recording a reading of signals from the muscle and/or nerve fibers, of at least one apparatus for acquiring muscle or biopotential signals, for signal conditioning, signal processing, sending, and receiving information, and self-adjusting feedback;
- B) Selecting at least one external computer and/or monitor or graphic interface for viewing external information and several recording parameters from said at least one apparatus for acquiring muscle or biopotential signals, for signal conditioning, for signal processing, sending, and receiving information, and self-adjusting feedback, which are, but are not limited to, sampling duration and/or time, session number, calibration, initial amplification value, type of user (with or without muscle damage), and injury;
- C) Recording the reference muscle or biopotential signals which, when first used, serve as a calibration parameter, wherein recording of the signals is achieved by implementing at least one differential mode amplifier, wherein the differential mode amplifier contains at least one potentiometer capable of modifying its impedance value z manually or electronically,
- D) Calculating, in a module for processing of the signals, a maximum value in the acquired muscle or biopotential signal samples during a reference cycle of contraction or electrical activity;
- E) If the maximum value does not exceed a calibration or preconfigured or selected minimum threshold from the computer system and/or monitor or graphic interface for viewing external information, then
- F) Adjusting the potentiometer gain, (Vin) (1+|z|),
wherein Vin is the voltage of the acquired muscle or biopotential signal samples and the potentiometer gain is called digital control loop amplification;
- G) Re-recording the signals as in step C);
- H) Sending the information to the external computer and/or monitor or graphic interface, for viewing external information;
- I) Calculating a muscle assessment and monitoring indicator as a percentage increase or decrease of a difference between the calibration or selected minimum threshold and the maximum value of the current sample muscle or biopotential signal divided by the calibration minimum threshold;
- J) Applying a variety of finite impulse response (FIR) and/or infinite impulse response (IIR) type filters for averaging of the muscle assessment and monitoring indicator;
- K) Calculating the indicator by means of calculation of discrete integrals of percentage increase or decrease of the difference; and
- L) Applying machine learning or deep learning techniques to develop optimizations of use, therapies, or exercises.

15. The method of claim 14, wherein the method provides at least one indicator of muscle assessment or electrical activity.

16. The method of claim 15, wherein the at least one indicator of muscle assessment or electrical activity selected based on improvement or deterioration of the muscle condition.

17. The method of claim 14, wherein the method extracts the muscle assessment and monitoring indicator, and parameters related to muscle assessment and electrical activity.

18. The method of claim 14, wherein the method implements neural networks by supervised and/or unsupervised learning, convolutional networks, diffuse and/or neurodiffuse systems, parametric identification and/or non-parametric identification, linear or polynomial regressions among others.

19. The method of claim 14, wherein the at least two or more biopotential signal sensors are surface mount electrodes.

20. The method of claim 19, wherein the at least two or more biopotential signal sensors are non-invasive.

* * * * *